(12) United States Patent
Frisby et al.

(10) Patent No.: US 9,194,730 B2
(45) Date of Patent: Nov. 24, 2015

(54) METHOD AND APPARATUS FOR DETERMINING THE PHASE COMPOSITIONS OF A MULTIPHASE FLUID FLOW

(75) Inventors: Ben Frisby, Gloucestershire (GB); Jeremy Miller, Goucestershire (GB)

(73) Assignee: Spirax-Sarco Limited, Gloucestershire (GB)

( * ) Notice: Subject to any disclaimer, the term of this patent is extended or adjusted under 35 U.S.C. 154(b) by 412 days.

(21) Appl. No.: 13/619,080

(22) Filed: Sep. 14, 2012

(65) Prior Publication Data

US 2013/0068035 A1 Mar. 21, 2013

(30) Foreign Application Priority Data

Sep. 14, 2011 (GB) .................................. 1115913.4
Jul. 11, 2012 (GB) .................................. 1212342.8

(51) Int. Cl.
*G01F 1/66* (2006.01)
*G01F 1/74* (2006.01)
*G01N 29/036* (2006.01)
(Continued)

(52) U.S. Cl.
CPC .. *G01F 1/74* (2013.01); *G01F 1/66* (2013.01); *G01N 29/022* (2013.01); *G01N 29/036* (2013.01); *G01N 29/46* (2013.01); *G01N 2291/02425* (2013.01); *G01N 2291/02845* (2013.01); *G01N 2291/105* (2013.01)

(58) Field of Classification Search
CPC .......... G01N 2291/02425; G01N 2291/02845; G01N 2291/101; G01N 29/022; G01N 29/46; G01F 1/66; G01F 1/74

USPC ........................... 127/29, 67; 44/307; 702/19
See application file for complete search history.

(56) References Cited

U.S. PATENT DOCUMENTS

| | | | |
|---|---|---|---|
| 4,135,395 A | * | 1/1979 | Sullivan et al. ............ 73/861.21 |
| 4,674,337 A | | 6/1987 | Jonas |

(Continued)

FOREIGN PATENT DOCUMENTS

| | | |
|---|---|---|
| CN | 1731143 | 2/2006 |
| GB | 12615 | 0/1960 |

(Continued)

OTHER PUBLICATIONS

European Patent Application No. 1212342.8; Search Report under Section 17 completed on Aug. 2, 2012 (2 pages).

(Continued)

*Primary Examiner* — John Fitzgerald
(74) *Attorney, Agent, or Firm* — Banner & Witcoff, Ltd.

(57) ABSTRACT

Systems and methods are provided that relate to determining the phase compositions of a multiphase fluid flow in a fluid line, including determining a flow velocity parameter which is related to the flow velocity of the fluid flow in the fluid line using a flow sensor and obtaining a vibration signal from the fluid flow using a vibration sensor comprising a target disposed in the fluid flow which vibrates in response to fluid flow in the fluid line. The signal may be analyzed to determine an energy parameter which is related to the energy of the vibration signal within a frequency band, and a phase composition parameter, such as a dryness parameter, relating to the phase compositions of the fluid flow is determined using the flow velocity parameter and the energy parameter. An apparatus for determining the phase compositions of a multiphase fluid flow in a fluid line is disclosed.

20 Claims, 7 Drawing Sheets

(51) Int. Cl.
*G01N 29/46* (2006.01)
*G01N 29/02* (2006.01)

(56) References Cited

U.S. PATENT DOCUMENTS

| | | | |
|---|---|---|---|
| 4,824,016 A | | 4/1989 | Cody et al. |
| 4,832,503 A | * | 5/1989 | Dowling et al. ............... 374/42 |
| 5,035,146 A | | 7/1991 | Chien |
| 5,207,090 A | * | 5/1993 | Downing, Jr. ............... 73/61.75 |
| 5,257,530 A | * | 11/1993 | Beattie et al. ............... 73/61.75 |
| 5,415,048 A | * | 5/1995 | Diatschenko et al. ..... 73/861.04 |
| 5,503,035 A | * | 4/1996 | Itoh et al. ................... 73/861.23 |
| 5,524,475 A | * | 6/1996 | Kolpak et al. ............... 73/19.03 |
| 5,571,974 A | * | 11/1996 | Nauful ....................... 73/861.27 |
| 6,813,962 B2 | * | 11/2004 | Gysling et al. ............. 73/861.26 |
| 6,988,857 B2 | * | 1/2006 | Kroemmer et al. ............ 406/34 |
| 8,683,874 B2 | * | 4/2014 | Limacher et al. .......... 73/861.24 |
| 2003/0235263 A1 | * | 12/2003 | Rajendran et al. ............ 376/248 |
| 2008/0257066 A1 | * | 10/2008 | Henry et al. ............. 73/861.356 |
| 2008/0282781 A1 | | 11/2008 | Hemblade |
| 2009/0120168 A1 | | 5/2009 | Harrison et al. |

FOREIGN PATENT DOCUMENTS

| | | |
|---|---|---|
| JP | 56125621 | 10/1981 |
| JP | 62009253 | 1/1987 |
| WO | 2010103003 A2 | 9/2010 |

OTHER PUBLICATIONS

European Patent Application No. 1115913.4; Search Report under Section 17 completed on Dec. 13, 2011 (2 pages).
Etchart et al. "MEMS sensors for density-viscosity sensing in a low-flow microfluidic environment," Sensors and Actuators, vol. 141, No. 2, Feb. 2, 2008, 10 pages.
European Patent Office, "European Search Report," issued in connection with European application serial No. 12184340.3, issued Jun. 16, 2014, 7 pages.

* cited by examiner

METHOD AND APPARATUS FOR DETERMINING THE PHASE COMPOSITIONS OF A MULTIPHASE FLUID FLOW

CROSS-REFERENCE TO RELATED APPLICATIONS

The present application claims priority to GB 1115913.4 filed on 14 Sep. 2011 and to GB 1212342.8 filed on 11 Jul. 2012, which are hereby incorporated by reference in their entirety for any and all purposes.

BACKGROUND

Aspects of the invention relate to a method and apparatus for determining the phase compositions of a multiphase fluid flow, in particular, although not exclusively, to a method and apparatus for determining the dryness of wet steam.

The use of steam as a heating medium in industrial processes is very widespread. Most process and heating steam systems use saturated wet steam which is a two-phase fluid comprising vapour as a first phase and condensate as a second phase.

It is often necessary to know the dryness, or quality, of the wet steam. Steam quality is the percentage of the mass of the fluid that is vapour, and therefore saturated steam has a steam quality of 100% and saturated liquid has a steam quality of 0%.

Some industrial processes have particular requirements regarding steam quality. For example, in sterilisation systems the steam quality must be between 95%-100%. This is set-out by standard BS EN 285 which specifies the requirements and relevant tests for large steam sterilisers primarily used in health care. Currently, steam quality is typically measured using throttling calorimetry. An example of an apparatus and method for measuring steam quality using a throttling calorimeter is disclosed in GB 1906 12,615. Whilst throttling calorimetry can be used to successfully determine the quality of steam, it is a time-consuming process and the apparatus is relatively complicated.

It is therefore desirable to provide an improved method and apparatus for determining the phase compositions of a multiphase fluid flow.

SUMMARY

Aspects of the invention concerns a method and apparatus for determining the phase compositions (which may be the dryness) of a multiphase fluid flow, such as wet steam, from the characteristics of a vibration signal obtained from the fluid flow, and a flow velocity parameter of the fluid flow.

According to an aspect of the invention there is provided a method of determining the phase compositions (which may be the dryness) of a multiphase fluid flow in a fluid line, comprising: determining a flow velocity parameter which is related to (or which is a function of) the flow velocity of the fluid flow in the fluid line using a flow sensor; obtaining a vibration signal from the fluid flow using a vibration sensor comprising a target disposed in the fluid flow which vibrates in response to fluid flow impact; analysing the vibration signal to determine an energy parameter which is related to the energy of the vibration signal within a frequency band; and determining a phase composition parameter (which may be a dryness parameter) relating to the phase compositions (which may be the dryness) of the fluid flow using the flow velocity parameter and the energy parameter. The phase composition parameter may be determined empirically from the flow velocity parameter and the energy parameter.

The flow velocity parameter may be expressed as a rate of change of distance (in meters per second for example), or may be a parameter that is a function of the actual flow velocity, for example, the rotational speed in the case of a turbine flow meter, or time in the case of an optical flow meter. The target may be a diaphragm. The vibration sensor may further comprise an electrical converter for converting the vibration of the target into a vibration signal. The electrical converter may comprise a piezoelectric transducer. The flow sensor and vibration sensor may be separate from one another. The frequency band may be a single frequency or a range of frequencies. The energy parameter may be any suitable parameter that can be derived or determined from the vibration signal and which can be related, in conjunction with a flow velocity parameter, to the phase compositions/dryness of the fluid flow.

In some embodiments, but not necessarily in all embodiments, the target may vibrate in response to fluid flow impact on the target. The target may be configured to resonate at one or more resonant frequencies. The vibration signal may be analysed to determine an energy parameter which is the amplitude of a resonant frequency of the vibration signal.

The flow velocity parameter may be determined at a first position and the vibration sensor may measure the vibration signal at a second position that is spaced from the first position in the longitudinal direction of the fluid line. The fluid flow may be mixed between the first and second positions. The fluid flow may be mixed by the flow sensor. This may help to ensure that the fluid flowing in the line is substantially uniform. The first position may be upstream of the second position.

The vibration sensor may measure the vibration signal in the time domain. Analysing the vibration signal may include transforming the vibration signal from the time domain to the frequency domain. The vibration signal may be transformed from the time domain to the frequency domain using a fast Fourier transform (FFT).

The energy parameter may be dependent on the phase compositions of the fluid flow and the flow velocity. In other words, the energy parameter may change in response to a change in either the flow velocity or the phase compositions of the fluid flow. The energy parameter may be the total energy of the vibration signal within the frequency band. This may be determined by summing the amplitudes of all of the frequencies within the frequency band. The energy parameter may be the amplitude of the peak frequency within the frequency band. In other embodiments, the energy parameter may be the average amplitude of all frequencies within the band, or any other suitable value capable of characterising the energy of the vibration signal within the frequency band.

The frequency band may be predetermined or fixed for a particular installation. Analysing the vibration signal may include defining the frequency band about a peak frequency. The method may include detecting the peak frequency. The frequency band may contain a peak frequency.

The method may further comprise determining a parameter relating to the temperature of the fluid flow. The phase composition and/or dryness parameter may be determined by using a flow velocity parameter, the temperature parameter and the energy parameter. The temperature parameter may be an actual temperature, or may be some other parameter that is related to temperature, for example pressure.

Determining a phase composition and/or a dryness parameter may comprise accessing a database containing data correlating flow velocity parameters and energy parameters with phase composition and/or dryness parameters. If the multiphase fluid is wet steam, the dryness parameter may be expressed as a percentage where 100% is saturated vapour and where 0% is saturated liquid. The dryness parameter may be known as "steam quality".

The method may further comprise outputting the phase composition and/or dryness parameter. Outputting the phase composition and/or dryness parameter may comprise displaying and/or transmitting the phase composition and/or dryness parameter. The phase composition and/or dryness parameter may be transmitted wirelessly.

The fluid flow may be a steam flow, such as wet steam. The dryness parameter may be known as the "vapour quality".

According to another aspect of the invention there is provided an apparatus for determining the phase compositions (which may be the dryness) of a multiphase fluid flow flowing in a fluid line, comprising: a flow sensor for determining a flow velocity parameter which is related to the flow velocity of the fluid flow in the fluid line; a vibration sensor comprising a target arranged to be disposed in the fluid flow which vibrates in response to fluid flow in the fluid line for obtaining a vibration signal from the fluid flow; a vibration signal analysis unit for analysing the vibration signal to determine an energy parameter which is related to the energy of the vibration signal within a frequency band; and a phase composition determining unit (which may be a dryness determining unit) for determining a phase composition parameter (which may be a dryness parameter) relating to the phase compositions (which may be the dryness) of the fluid flow using the flow velocity parameter and the energy parameter.

The flow sensor may be arranged to determine the flow velocity parameter at a first position and the vibration sensor may be arranged to measure the vibration signal at a second position that is spaced from the first position in the longitudinal direction of the fluid line. The apparatus may further comprise a fluid mixer for mixing the fluid flow between the first and second positions. The mixer may be part of the flow sensor. Alternatively, the mixer may be disposed between the flow sensor and the vibration sensor. The first position may be upstream of the second position.

The vibration sensor may be arranged to measure the vibration signal in the time domain. The vibration signal analysis unit may be arranged to transform the vibration signal from the time domain to the frequency domain. The vibration signal analysis unit may be arranged to transform the vibration signal from the time domain to the frequency domain using a fast Fourier transform (FFT).

The energy parameter may be dependent on the phase compositions of the fluid flow and the flow velocity. The energy parameter may be the total energy of the vibration signal within the frequency band. The energy parameter may be the amplitude of the peak frequency within the frequency band. The frequency band may be predetermined. The vibration signal analysis unit may be arranged to define the frequency band about a peak frequency. The frequency band may contain a peak frequency.

The apparatus may further comprise a database containing data correlating flow velocity parameters and energy parameters with phase composition and/or dryness parameters. The phase composition and/or dryness determining unit may be arranged to access the database so as to determine a phase composition and/or a dryness parameter relating to the phase compositions and/or dryness of the fluid flow.

The apparatus may further comprise an outputting unit for outputting the phase composition and/or dryness parameter. The outputting unit may comprise a display for displaying the phase composition and/or dryness parameter and/or a transmitter for transmitting the phase composition and/or dryness parameter.

The apparatus may be arranged to determine the phase compositions and/or the dryness of a steam flow.

The flow sensor may comprise a sensor that is arranged to measure a flow parameter which is related to flow velocity. The apparatus may further comprise a length of pipe having connectors at either end, wherein the sensor and target are longitudinally spaced from one another and disposed within the pipe. A fluid mixer may be disposed within the pipe in between the sensor and the target. The distance between the connectors may be in accordance within a predetermined standard.

The target may be a diaphragm. In some embodiments the target may be arranged to resonate in response to fluid flow impact. The vibration sensor may further comprise an electrical converter for converting the vibration of the target into a vibration signal. The electrical converter may comprise a piezoelectric transducer.

Aspects of the invention also concern a steam system comprising an apparatus in accordance with any statement herein.

According to another aspect of the invention there is provided a method of determining the phase compositions/dryness of a multiphase fluid flow, comprising: determining a flow velocity parameter which is related to the flow velocity of the fluid flow using a flow sensor; obtaining a vibration signal from the fluid flow using a vibration sensor comprising a target disposed in the fluid flow which vibrates in response to fluid flow or fluid flow impact; analysing the vibration signal to determine a vibration signal parameter; and determining a phase composition/dryness parameter relating to the phase compositions/dryness of the fluid flow using the flow velocity parameter and the vibration signal parameter. The vibration signal parameter may be any suitable parameter that can be derived or determined from the vibration signal and which can be related, in conjunction with a flow velocity parameter, to the phase compositions/dryness of the fluid flow. The vibration signal parameter may be the amplitude of a resonant frequency of the vibration signal.

According to yet another aspect of the invention there is provided an apparatus for determining the phase compositions/dryness of a multiphase fluid flow flowing in a fluid line, comprising: a flow sensor for determining a flow velocity parameter which is related to the flow velocity of the fluid flow; a vibration sensor comprising a target arranged to be disposed in the fluid flow which vibrates in response to fluid flow or fluid flow impact for obtaining a vibration signal from the fluid flow; a vibration signal analysis unit for analysing the vibration signal to determine a vibration signal parameter; and a phase composition/dryness determining unit for determining a phase composition/dryness parameter relating to the phase compositions/dryness of the fluid flow using the flow velocity parameter and the vibration signal parameter.

The invention may comprise any combination of the features and/or limitations referred to herein, except combinations of such features as are mutually exclusive.

BRIEF DESCRIPTION OF THE DRAWINGS

Embodiments of the invention will now be described, by way of example, with reference to the accompanying drawings, in which:

FIG. 4b is an enlarged view of the active area depicted on the left side of FIG. 4a, and FIG. 4c is an enlarged view of the active area depicted on the right side of FIG. 4a.

DETAILED DESCRIPTION

Figure 1:
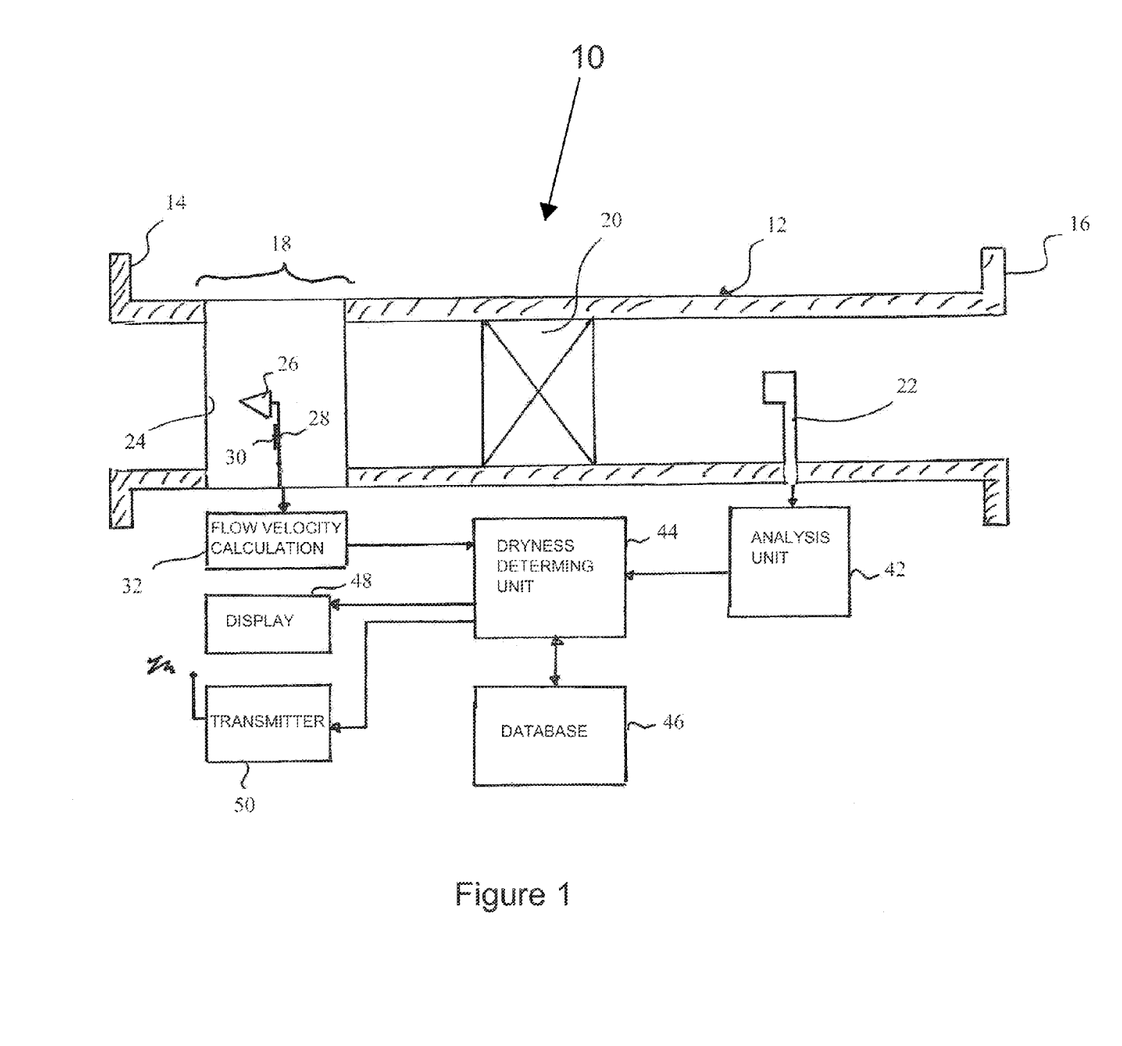
FIG. 1 schematically shows an apparatus for determining the dryness of wet steam flowing in a steam line.

FIG. 1 shows generally at 10 an apparatus for determining the phase compositions of wet steam flowing in a steam line. In this particular embodiment the apparatus 10 is arranged to determine the dryness of the wet steam. The apparatus 10 comprises a length of pipe 12 having connection flanges 14, 16 at either end. The apparatus 10 further comprises a flow meter (or sensor) 18 for determining the flow velocity of the steam, a fluid mixer 20 for mixing the steam flow, and a vibration sensor 22 for obtaining a vibration signal from the steam flow.

The flow meter 18 comprises a sensor 24 disposed in the pipe 12 for measuring a flow velocity parameter that is related to and can therefore be converted into a flow velocity, and a flow velocity calculation unit 32 for calculating (or estimating) the flow velocity from the measured flow velocity parameter. In this embodiment the sensor 24 comprises a cone 26 mounted to a cantilevered arm 28 which has a strain gauge mounted thereto 30. The cantilevered arm 28 bends in response to the flow velocity and induces a strain in the strain gauge 30. The electrical resistance of the strain gauge 30 is output to the flow velocity calculation unit 32 as a flow velocity parameter, and the unit 32 calculates the flow velocity from the measured electrical resistance representing the strain of the cantilevered arm 28. It should be appreciated that the flow meter 18 may be any suitable type of flow meter, such as a turbine flow meter, an optical flow meter, a variable area flow meter, a spring loaded variable area flow meter, a direct in-pipe variable area flow meter, a pilot tube flow meter or a vortex shedding flow meter. Although it has been described that the measured flow velocity parameter, for example the resistance of the strain gauge, is converted into a flow velocity using the calculation unit 32, it should be appreciated that it is possible to use the raw flow velocity parameter value instead.

Figure 2:
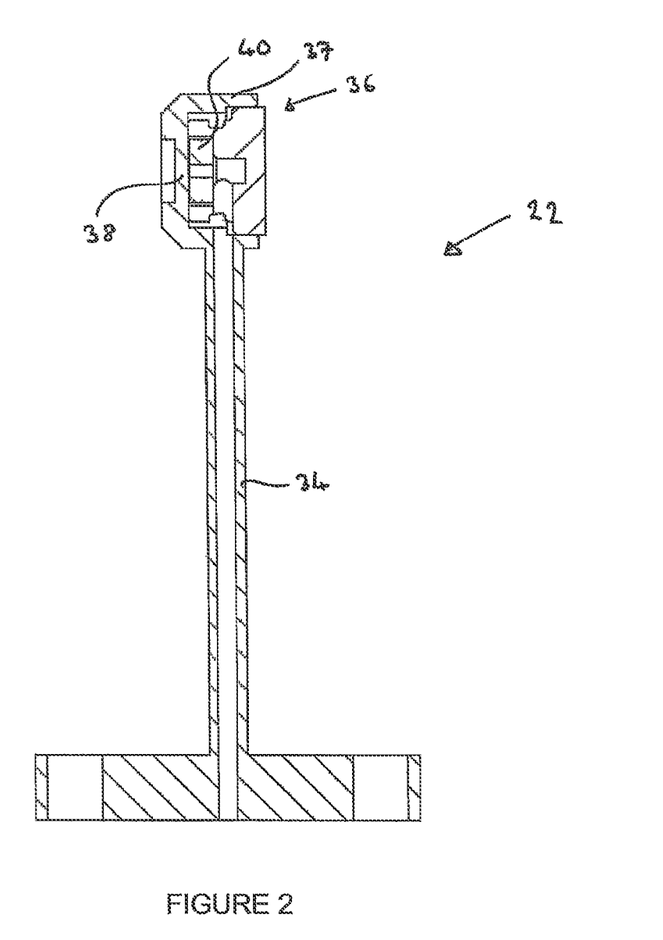
FIG. 2 schematically shows the vibration sensor of FIG. 1.

The vibration sensor 22 is disposed within the pipe 12 downstream of the flow meter sensor 24 in the longitudinal direction of the pipe 12 and is shown in more detail in FIG. 2. The vibration sensor 22 comprises a hollow stem 34 that extends into the pipe and a head 36 which is mounted onto the end of the stem 34 and which is aligned with the axis of the pipe. The head 36 comprises a body 37 and a substantially planar target 38 which is in the form of a diaphragm. The target 38 faces the steam flow and lies in a plane perpendicular to the steam flow direction. The target 38 is arranged to vibrate in response to fluid flow within the pipe. A piezoelectric transducer 40 is mounted within the body 37 and is coupled to the target 38 such that vibration of the target 38 in the axial direction is converted into an electrical vibration signal. Signal wires (not shown) are connected to the piezoelectric transducer 40 and pass down the hollow stem 34 to extend to the outside of the pipe 12. The stem 34 and head 36 are manufactured from stainless steel and the diaphragm target 38 is a thin metallic plate.

In this embodiment the apparatus 10 is an integrated unit which can be easily installed in a new steam installation, or can be retrofitted to an existing steam installation, by connecting the flanges 14, 16 to corresponding connection flanges of a steam line such that the pipe 12 forms part of the steam line 12. However, it should be appreciated that in other embodiments the apparatus may be supplied as a series of separate components that must be installed and wired together individually.

In use, the fluid flow within the steam line causes the target 38 to vibrate in the axial direction. If the fluid is wet steam, the fluid flow contains both water droplets and vapour. The characteristics of the vibration of the target 38 are related to both the dryness of the steam and the flow velocity. Therefore, by using the flow velocity determined by the flow meter 18, the apparatus 10 can determine the dryness of the steam. In order to ensure that the fluid flow is substantially uniform across the cross-sectional area of the pipe 12, a fluid mixer 20 is disposed in the pipe 12 between the flow meter sensor 24 and the vibration sensor 22. The fluid mixer 20 helps to ensure that no condensate slugs pass under the vibration sensor 22 which would lead to the apparatus determining a steam dryness value higher than the actual value.

Figure 3:
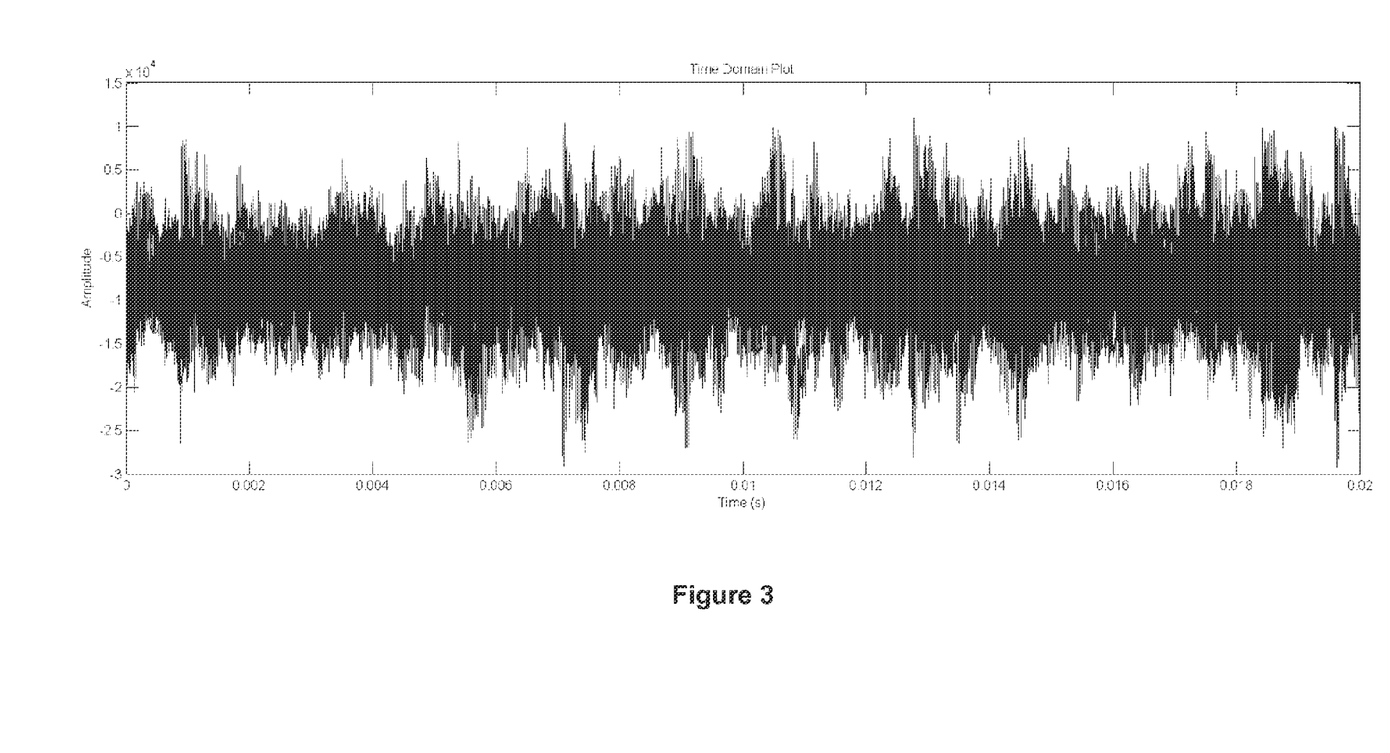
FIG. 3 schematically shows a vibration signal obtained by the vibration sensor in the time domain.
Figure 4A:
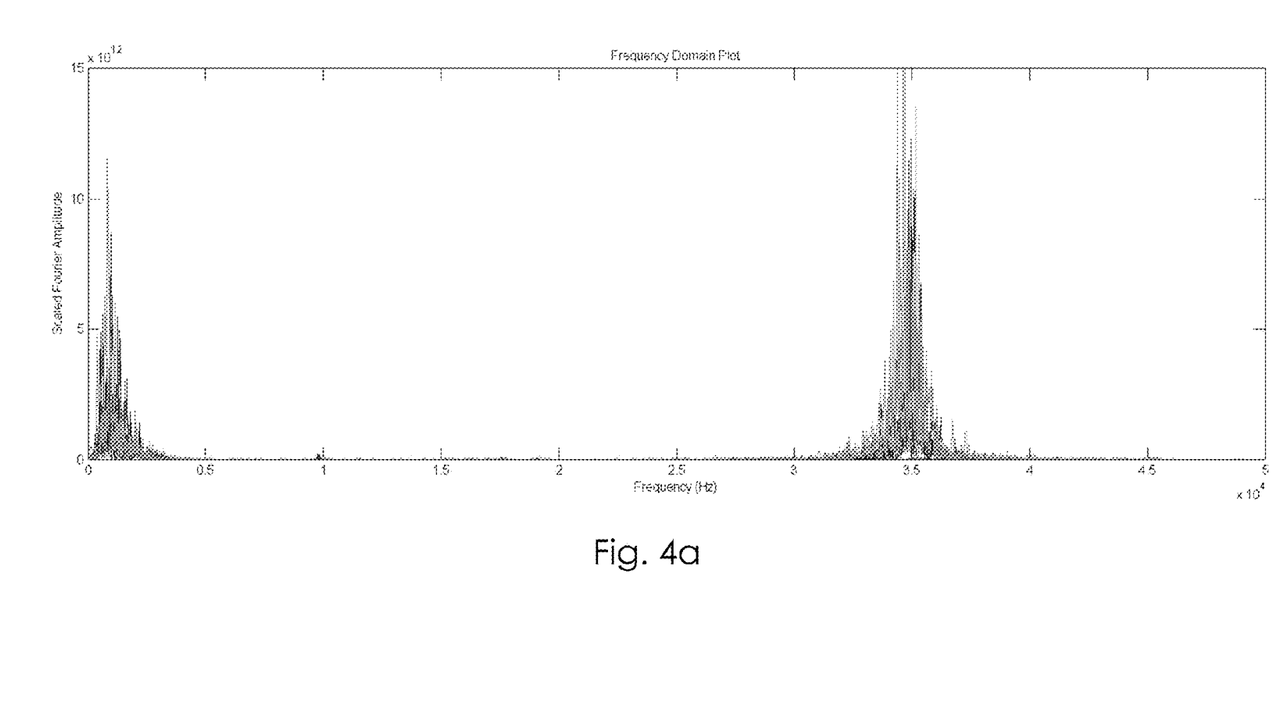
FIG. 4a schematically shows three vibration signals obtained by the vibration sensor in the frequency domain.
Figure 4B:
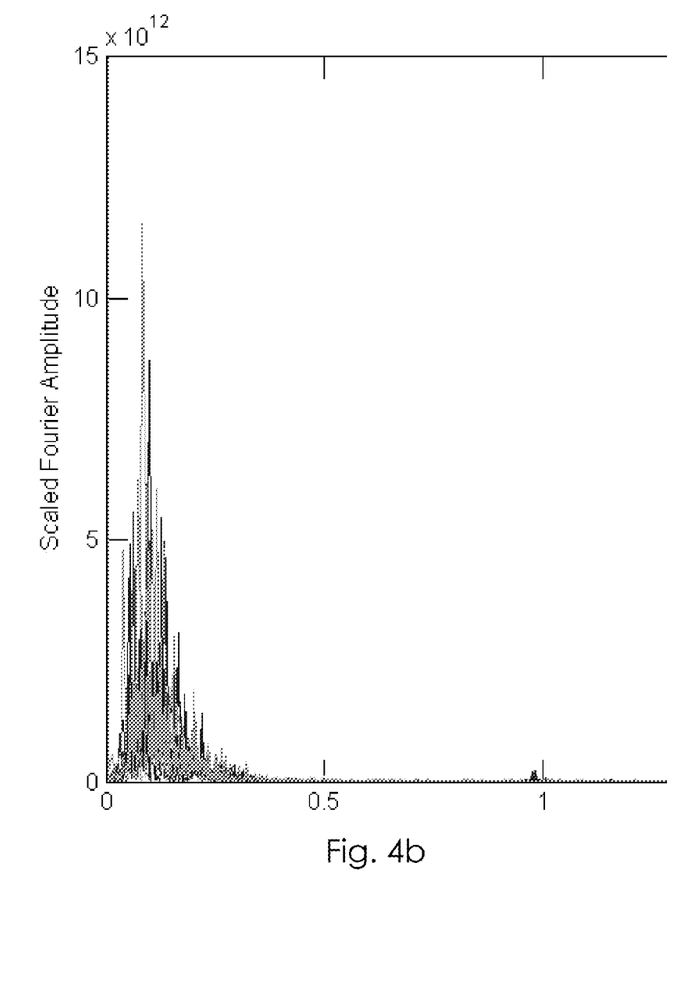
Figure 4C:
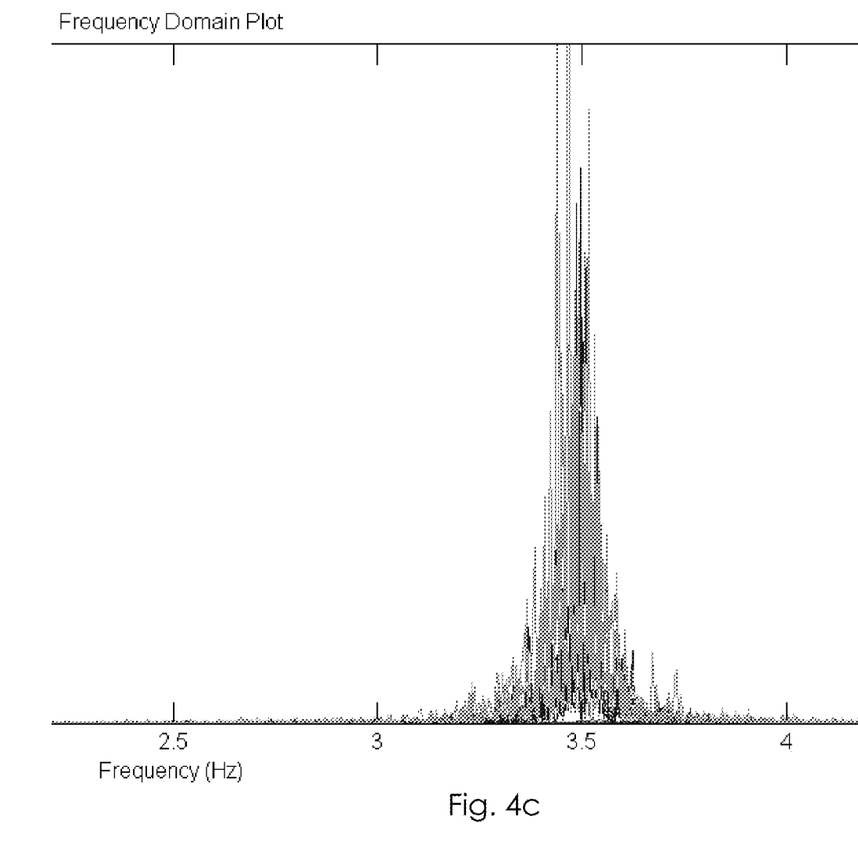

The vibration sensor 22 outputs the electrical vibration signal in the time domain and a graphical representation of such a signal is shown in FIG. 3. This vibration signal is output to a vibration signal analysis unit 42. The analysis unit 42 transforms the vibration signal from the time domain to the frequency domain using a fast Fourier transform (FFT) algorithm. A graphical representation of three different vibration signals in the frequency domain is shown in FIGS. 4a-4c. The three different vibration signals correspond to three different steam flows having different steam dryness values. As can be seen from FIG. 4a, the target 38 vibrates at a peak frequency that is substantially the same for all three dryness values. However, the energy of the vibration signal (i.e. the amplitude of the peak frequency) changes depending on the steam dryness value.

After transforming the vibration signal to the frequency domain, the analysis unit 42 determines the energy of the vibration signal within a predefined frequency band B. This is done by summing the individual amplitudes of all of the individual frequencies within the frequency band B. In this particular embodiment the frequency band is 26-46 kHz. However, it should be appreciated that other frequency bands may be used, as the frequency band may depend on the particular construction of the vibration sensor and the steam installation as a whole. The energy of the vibration signal within the frequency band is termed an "energy parameter". The energy parameter is dependent on both the phase compositions, or steam dryness value, of the steam flow, and the flow velocity of the steam flow.

In this embodiment the frequency band is defined as a range of frequencies, but in other embodiments the frequency band could be a single frequency. However, if a FFT is used to transform the vibration signal from the time domain to the frequency domain, if the frequency band is defined as a single frequency this will in fact correspond to a range of frequencies defined by the resolution of the FFT. The frequency band can be fixed for a particular installation as the peak frequency is substantially independent of the flow velocity and dryness. However, it may be necessary to change the frequency band if the installation changes. In other embodiments, the analysis unit 42 may identify a peak frequency, and define the frequency band about this peak frequency.

Although it has been described that the energy parameter is the energy of the vibration signal within a frequency band, the energy parameter may be any suitable parameter that is related to the energy of the vibration signal and which can be related in conjunction with a flow velocity parameter, to the dryness of the steam. For example, the energy parameter may be the amplitude of the peak frequency, the average amplitude of the frequencies within the frequency band, or any other suitable value.

The energy parameter determined by the vibration signal analysis unit 42 and the flow velocity calculated by the flow velocity calculation unit 32 are output to a dryness determining unit 44. The dryness determining unit 44 takes the two values and accesses a database 46 in order to empirically determine the dryness of the steam. The database 46 contains a look-up table that contains reference or calibration data that correlates a range of flow velocities and energy parameters with steam dryness values. The reference or calibration data is data obtained by experimentation. The determining unit 44 determines the steam dryness value from the data in the look-up table and displays this dryness value on a local display 48. In addition to this, the dryness value is transmitted to a control room via a wireless connection using a wireless transmitter 50. This allows the steam dryness to be remotely monitored. It should be appreciated that the look-up table may contain data that correlates a range of flow velocity parameters (as opposed to flow velocities) and energy parameters with steam dryness values. As opposed to determining and outputting a dryness parameter, other parameters that express the phase compositions of the multiphase flow may be determined and output.

The dryness determining unit 44 is also configured to calculate the mass flow rate of the steam flow based on the steam dryness value and the flow velocity. The mass flow rate may also be displayed on the display 48 and may also be transmitted using the transmitter 50.

The look-up table contained within the database 46 is created empirically. It may be necessary to create a new look-up table for each apparatus 10. However, it may be possible to produce a generic look-up table suitable for all apparatuses. In order to create the look-up table, a series of pre-determined volumes of water are injected into the steam line at range of flow velocities and for each combination of water volume/velocity the energy parameter of the vibration sensor 22 is recorded. The steam quality (or dryness) can be calculated from the known water volume and therefore by this calibration method a look-up table providing correlations between various energy parameters and flow velocities with dryness can be created.

Although the peak frequency of the target 38 remains substantially constant regardless of steam dryness, slight variations may occur in the peak frequency if a film of water, for example, builds up on the face of the target 38. Further, a change in temperature of the target 38 may cause its mechanical properties to change which may also result in the peak frequency shifting. It may be possible to determine the temperature of the steam from the peak frequency.

In some arrangements it is possible that the energy parameter is a function of the temperature, as well as of the dryness and flow velocity. If this is the case, a temperature sensor may be provided to measure the temperature of the steam. In such an arrangement the database 46 would contain a "three-dimensional" look-up table correlating flow velocity, energy parameter and temperature with dryness parameters. Instead of using a temperature sensor, it may be possible to use a pressure sensor and calculate (or estimate) the temperature from this, or the temperature (or pressure) may be determined from the resonant frequency.

Figure 5:
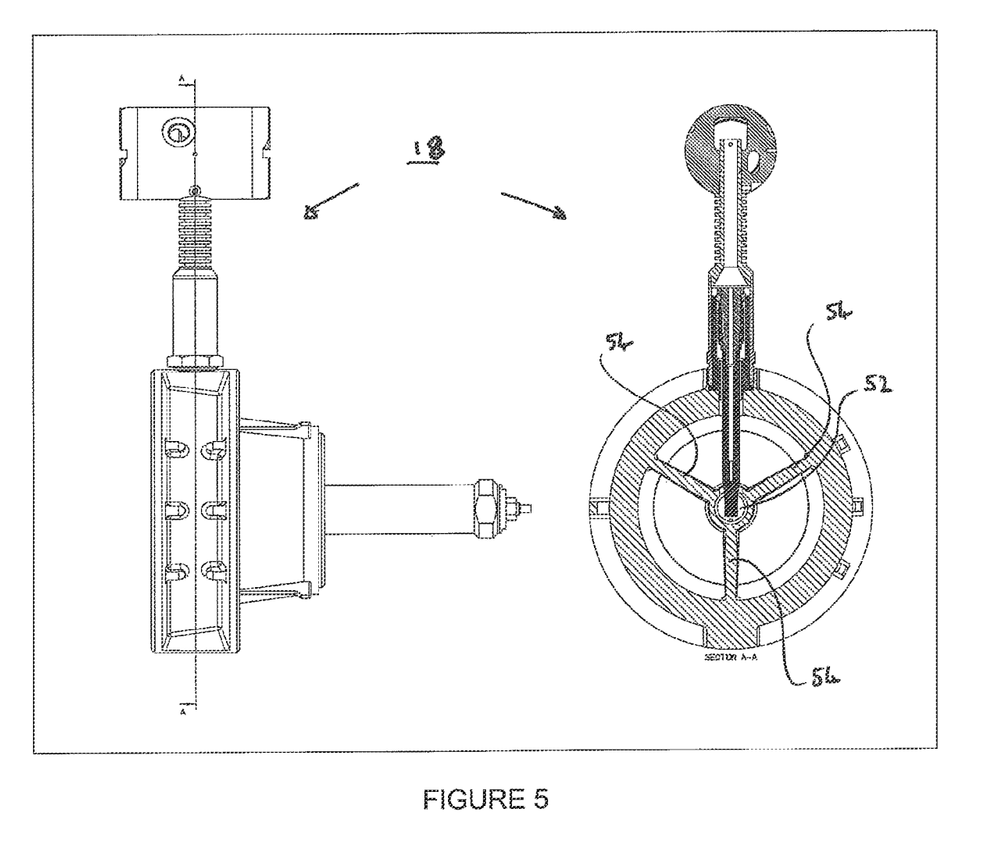
FIG. 5 schematically shows a direct in-line variable area flow meter that can be used with the apparatus of FIG. 1.

Although it has been described that a mixer 20 is disposed in the steam pipe 12 between the flow sensor 18 and the vibration sensor 22, it may be possible to incorporate the flow mixer into the flow sensor 18. FIG. 5 shows a direct in-line variable area (DIVA) flow meter 18 that can be installed in a steam line 12. The flow meter 18 comprises a cone 52 that is supported at the centre of the line 12 using three radially extending spokes 54. These spokes 54 can be configured as mixing vanes such that as the fluid flow passes through the flow meter 18 the fluid is mixed. An example of a DIVA flow meter is described in our earlier European Patent Number 0593164.

In the embodiments described above the vibration signal is analysed to determine an energy parameter and this, together with a flow velocity parameter, is used to determine the dryness of the fluid. However, it should be appreciated that the vibration signal could be analysed in a different manner to determine another vibration signal parameter which can be used together with a flow velocity parameter to determine the dryness of the fluid. For example, the vibration signal could be processed to detect individual fluid droplet impact events and this could be averaged to provide a vibrational signal parameter in the form of a droplet impact parameter. This droplet impact parameter, derived from the vibrational signal, could then be used in conjunction with a flow velocity parameter to determine the dryness of the fluid.

Although it has been described that the method and apparatus can be used for measuring the dryness of steam, it should be appreciated that the method and apparatus are also suitable for measuring the dryness of any other multiphase fluid flow.

What is claimed is:

1. A method of determining the phase compositions of a multiphase fluid flow in a fluid line, comprising:
    determining a flow velocity parameter which is related to the flow velocity of the fluid flow in the fluid line using a flow sensor;
    obtaining a vibration signal from the fluid flow using a vibration sensor comprising a target disposed in the fluid flow which vibrates in response to fluid flow in the fluid line;
    analysing the vibration signal to determine an energy parameter which is related to the energy of the vibration signal within a frequency band; and
    determining a phase composition parameter relating to the phase compositions of the fluid flow using the flow velocity parameter and the energy parameter.

2. A method according to claim 1, wherein the phase composition parameter is a dryness parameter relating to the dryness of the fluid flow.

3. A method according to claim 1, wherein the energy parameter is dependent on the phase compositions of the fluid flow and the flow velocity.

4. A method according to claim 1, wherein the energy parameter is the total energy of the vibration signal within the frequency band.

5. A method according to claim 1, wherein the energy parameter is the amplitude of the peak frequency within the frequency band.

6. A method according to claim 1, wherein the frequency band is predetermined.

7. A method according to claim 1, wherein analysing the vibration signal includes defining the frequency band about a peak frequency.

8. A method according to claim 1, wherein the frequency band contains a peak frequency.

9. A method according to claim 1, wherein determining a phase composition parameter comprises accessing a database containing data correlating flow velocity parameters and energy parameters with phase composition parameters.

10. A method according to claim 1, wherein the fluid flow is a steam flow.

11. A method according to claim 1, further comprising outputting the phase composition parameter.

12. A method according to claim 11, wherein outputting the phase composition parameter comprises displaying and/or transmitting the phase composition parameter.

13. A method according to claim 1, wherein the flow velocity parameter is determined at a first position and wherein the vibration sensor measures the vibration signal at a second position that is spaced from the first position in the longitudinal direction of the fluid line.

14. A method according to claim 13, further comprising mixing the fluid flow between the first and second positions.

15. A method according to claim 13, wherein the first position is upstream of the second position.

16. A method according to claim 1, wherein the vibration sensor measures the vibration signal in the time domain.

17. A method according to claim 16, wherein analysing the vibration signal includes transforming the vibration signal from the time domain to the frequency domain.

18. A method according to claim 17, wherein the vibration signal is transformed from the time domain to the frequency domain using a fast Fourier transform (FFT).

19. A method of determining the dryness of a steam flow flowing in a fluid line, comprising:
   determining a flow velocity parameter which is related to the flow velocity of the steam flow in the fluid line using a flow sensor;
   obtaining a vibration signal in the time domain from the steam flow using a vibration sensor comprising a target disposed in the steam flow which vibrates in response to steam flow in the fluid line;
   wherein the flow velocity parameter is determined at a first position and wherein the vibration sensor measures the vibration signal at a second position that is spaced downstream from the first position in the longitudinal direction of the fluid line
   analysing the vibration signal by transforming it to the frequency domain and determining an energy parameter which is the total energy of the vibration signal within a fixed frequency band; and
   empirically determining a dryness parameter relating to the dryness of the steam flow by accessing a database containing data correlating flow velocity parameters and energy parameters with dryness parameters.

20. An apparatus for determining the dryness of a steam flow flowing in a fluid line, comprising:
   a length of pipe having connectors at either end for attachment to upstream and downstream portions of the fluid line;
   a flow sensor disposed within the pipe at a first position for determining a flow velocity parameter which is related to the flow velocity of the steam flow in the fluid line;
   a vibration sensor comprising a target disposed within the pipe at a second position spaced downstream from the first position and which is arranged to vibrate in response to steam flow in the fluid line so as to obtain a vibration signal in the time domain from the steam flow;
   a vibration signal analysis unit arranged to transform the vibration signal to the frequency domain and determine an energy parameter which is the total energy of the vibration signal within a fixed frequency band;
   a database containing data correlating flow velocity parameters and energy parameters with dryness parameters; and
   a dryness determining unit for empirically determining a dryness parameter relating to the dryness of the steam flow by accessing the database so as to determine a dryness parameter of the steam flow using the flow velocity parameter and the energy parameter.

* * * * *